(12) United States Patent
Lund

(10) Patent No.: US 9,622,848 B2
(45) Date of Patent: Apr. 18, 2017

(54) URETHRAL STENT SYSTEM AND METHOD

(75) Inventor: Jonathan J. Lund, Minneapolis, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 693 days.

(21) Appl. No.: 13/403,795

(22) Filed: Feb. 23, 2012

(65) Prior Publication Data

US 2012/0238803 A1    Sep. 20, 2012

Related U.S. Application Data

(60) Provisional application No. 61/445,699, filed on Feb. 23, 2011.

(51) Int. Cl.
*A61F 2/04*    (2013.01)
*A61F 2/00*    (2006.01)

(52) U.S. Cl.
CPC .............. *A61F 2/04* (2013.01); *A61F 2/0009* (2013.01); *A61F 2002/047* (2013.01)

(58) Field of Classification Search
CPC .. A61F 2/82–2/97; A61F 2002/821–2002/828; A61F 2002/8483; A61F 2002/8486; A61F 2002/915–2002/91591; A61F 2/0004–2/0027; A61M 1/1096; A61M 5/16881; A61M 2005/3128; A61M 2025/0076; A61M 2039/242–2039/2486
USPC ................................................ 600/29–32, 37
See application file for complete search history.

(56) References Cited

U.S. PATENT DOCUMENTS

| | | |
|---|---|---|
| 3,124,136 A | 3/1964 | Usher |
| 3,182,662 A | 5/1965 | Shirodkar |
| 3,384,073 A | 5/1968 | Van Winkle, Jr. |
| 3,472,232 A | 10/1969 | Earl |
| 3,789,828 A | 2/1974 | Schulte |
| 3,924,633 A | 12/1975 | Cook et al. |
| 4,019,499 A | 4/1977 | Fitzgerald |
| 4,172,458 A | 10/1979 | Pereyra |
| 4,857,041 A | 8/1989 | Annis et al. |
| 4,865,031 A | 9/1989 | O'Keeffe |
| 4,920,986 A | 5/1990 | Biswas |

(Continued)

FOREIGN PATENT DOCUMENTS

| | | |
|---|---|---|
| DE | 10211360 | 9/2003 |
| EP | 0248544 A1 | 12/1987 |

(Continued)

OTHER PUBLICATIONS

Bergman, et. al., "Three Surgical Procedures for Genuine Stress Incontinence: Five-Year Follow-up of a Prospective Randomized Study," Am. J. Obstetrics and Gynecology, vol. 173, No. 1, pp. 66-71.

(Continued)

*Primary Examiner* — Catherine B Kuhlman
(74) *Attorney, Agent, or Firm* — Seager, Tufte & Wickhem, LLP

(57) ABSTRACT

A urethral stent device comprising a mechanical valve system is provided. The urethral stent device can be delivered up through the urethra via a flexible delivery tool. The valve mechanism is adapted to open when exposed to a certain amount of intraluminal pressure and can remain open until a desired cessation of fluid flow is achieved.

14 Claims, 4 Drawing Sheets

(56) References Cited

U.S. PATENT DOCUMENTS

| | | |
|---|---|---|
| 4,938,760 A | 7/1990 | Burton et al. |
| 5,007,894 A | 4/1991 | Enhorning |
| 5,012,822 A | 5/1991 | Schwarz |
| 5,013,292 A | 5/1991 | Lemay |
| 5,019,032 A | 5/1991 | Robertson |
| 5,036,867 A | 8/1991 | Biswas |
| 5,112,344 A | 5/1992 | Petros |
| 5,123,428 A | 6/1992 | Schwarz |
| 5,256,133 A | 10/1993 | Spitz |
| 5,269,783 A | 12/1993 | Sander |
| 5,328,077 A | 7/1994 | Lou |
| 5,366,506 A * | 11/1994 | Davis .................... 623/23.66 |
| 5,386,836 A | 2/1995 | Biswas |
| 5,474,518 A | 12/1995 | Velaquez |
| 5,518,504 A | 5/1996 | Polyak |
| 5,582,188 A | 12/1996 | Benderev et al. |
| 5,591,163 A | 1/1997 | Thompson |
| 5,611,515 A | 3/1997 | Benderev et al. |
| 5,697,931 A | 12/1997 | Thompson |
| 5,782,916 A | 7/1998 | Pintauro et al. |
| 5,785,640 A | 7/1998 | Kresch et al. |
| 5,836,314 A | 11/1998 | Benderev et al. |
| 5,836,315 A | 11/1998 | Benderev et al. |
| 5,840,011 A | 11/1998 | Landgrebe et al. |
| 5,860,425 A | 1/1999 | Benderev et al. |
| 6,010,447 A | 1/2000 | Kardjian |
| 6,022,312 A * | 2/2000 | Chaussy et al. .................. 600/29 |
| 6,027,523 A | 2/2000 | Schmieding |
| 6,030,393 A | 2/2000 | Corlew |
| 6,039,686 A | 3/2000 | Kovac |
| 6,042,534 A | 3/2000 | Gellman et al. |
| 6,042,536 A | 3/2000 | Tihon et al. |
| 6,048,351 A | 4/2000 | Gordon et al. |
| 6,050,937 A | 4/2000 | Benderev |
| 6,056,688 A | 5/2000 | Benderev et al. |
| 6,068,591 A | 5/2000 | Bruckner et al. |
| 6,074,341 A | 6/2000 | Anderson et al. |
| 6,077,216 A | 6/2000 | Benderev et al. |
| 6,110,101 A | 8/2000 | Tihon et al. |
| 6,117,067 A | 9/2000 | Gil-Vernet |
| 6,221,005 B1 | 4/2001 | Bruckner et al. |
| 6,302,840 B1 | 10/2001 | Benderev |
| 6,306,079 B1 | 10/2001 | Trabucco |
| 6,328,686 B1 | 12/2001 | Kovac |
| 6,334,446 B1 | 1/2002 | Beyar |
| 6,352,553 B1 | 3/2002 | van de Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,423,080 B1 | 7/2002 | Gellman et al. |
| 6,451,024 B1 | 9/2002 | Thompson et al. |
| 6,478,727 B2 | 11/2002 | Scetbon |
| 6,502,578 B2 | 1/2003 | Raz et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,638,210 B2 | 10/2003 | Berger |
| 6,638,211 B2 | 10/2003 | Suslian et al. |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,830,052 B2 | 12/2004 | Carter et al. |
| 6,881,184 B2 | 4/2005 | Zappala |
| 6,908,425 B2 | 6/2005 | Luscombe |
| 6,911,002 B2 | 6/2005 | Fierro |
| 6,932,759 B2 | 8/2005 | Kammerer |
| 6,936,052 B2 | 8/2005 | Gellman et al. |
| 6,960,160 B2 | 11/2005 | Browning |
| 7,014,607 B2 | 3/2006 | Gellman |
| 7,070,556 B2 | 7/2006 | Anderson |
| 7,083,568 B2 | 8/2006 | Neisz et al. |
| 7,083,637 B1 | 8/2006 | Tannhauser |
| 7,112,210 B2 | 9/2006 | Ulmsten et al. |
| 7,121,997 B2 | 10/2006 | Kammerer et al. |
| 7,131,944 B2 | 11/2006 | Jaquetin |
| 7,175,591 B2 | 2/2007 | Kaladelfos |
| 7,226,407 B2 | 6/2007 | Kammerer |
| 7,226,408 B2 | 6/2007 | Harari et al. |
| 7,229,453 B2 | 6/2007 | Anderson |
| 7,261,723 B2 | 8/2007 | Smith et al. |
| 7,297,102 B2 | 11/2007 | Smith et al. |
| 7,303,525 B2 | 12/2007 | Watschke et al. |
| 7,407,480 B2 | 8/2008 | Staskin et al. |
| 7,601,118 B2 | 10/2009 | Smith et al. |
| 7,611,454 B2 | 11/2009 | De Leval |
| 7,621,864 B2 | 11/2009 | Suslian et al. |
| 7,686,759 B2 | 3/2010 | Sater |
| 7,762,942 B2 | 7/2010 | Neisz et al. |
| 7,789,821 B2 | 9/2010 | Browning |
| 7,927,342 B2 | 4/2011 | rioux |
| 7,981,024 B2 | 7/2011 | Levy |
| 2001/0049467 A1 | 12/2001 | Lehe et al. |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2003/0010929 A1 | 1/2003 | Priewe et al. |
| 2003/0036676 A1 | 2/2003 | Scetbon |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2005/0000523 A1 | 1/2005 | Beraud |
| 2005/0004427 A1 | 1/2005 | Cervigni |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0277806 A1 | 12/2005 | Cristalli |
| 2006/0015010 A1 | 1/2006 | Jaffe et al. |
| 2006/0058578 A1 | 3/2006 | Browning |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0032757 A1 * | 2/2007 | Medow .................. A61M 39/22 604/9 |
| 2007/0078295 A1 | 4/2007 | landgrebe |
| 2008/0140218 A1 | 6/2008 | Staskin et al. |
| 2008/0300607 A1 | 12/2008 | Meade et al. |

FOREIGN PATENT DOCUMENTS

| | | |
|---|---|---|
| EP | 0470308 A1 | 2/1992 |
| EP | 0650703 A1 | 6/1994 |
| EP | 0643945 A2 | 7/1994 |
| EP | 1093758 A1 | 4/2001 |
| EP | 1342450 B1 | 9/2003 |
| FR | 2787990 A1 | 7/2000 |
| GB | 2268690 A | 1/1994 |
| GB | 2353220 A | 10/2000 |
| WO | WO9319678 A2 | 10/1993 |
| WO | WO9819606 A1 | 5/1998 |
| WO | WO9835616 A1 | 8/1998 |
| WO | WO9835632 A1 | 8/1998 |
| WO | WO0018319 A1 | 4/2000 |
| WO | WO0027304 A1 | 5/2000 |
| WO | WO0066030 A1 | 11/2000 |
| WO | WO0074594 A1 | 12/2000 |
| WO | WO0074613 A1 | 12/2000 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0228312 A1 | 4/2002 |
| WO | WO0228315 A2 | 4/2002 |
| WO | WO0230293 A1 | 4/2002 |

(56) References Cited

FOREIGN PATENT DOCUMENTS

| | | |
|---|---|---|
| WO | WO0232284 A2 | 4/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02089704 A2 | 11/2002 |
| WO | WO03047435 A1 | 6/2003 |
| WO | WO03075792 A1 | 9/2003 |
| WO | WO03092546 A2 | 11/2003 |
| WO | WO2004016196 A2 | 2/2004 |
| WO | WO2004017862 A2 | 3/2004 |
| WO | WO2005037132 A2 | 4/2005 |
| WO | WO2006015031 A2 | 2/2006 |
| WO | WO2006108145 A1 | 10/2006 |
| WO | WO2007014241 A1 | 2/2007 |
| WO | WO2007059199 A2 | 5/2007 |
| WO | WO2007097994 | 8/2007 |
| WO | WO2007137226 A2 | 11/2007 |
| WO | WO2007149348 A2 | 12/2007 |
| WO | WO200714955542 | 12/2007 |
| WO | WO2008057261 A2 | 5/2008 |
| WO | WO2008124056 A1 | 10/2008 |
| WO | WO2009005714 A2 | 1/2009 |
| WO | WO2011/082350 | 7/2011 |

OTHER PUBLICATIONS

Blaivas et. al., "Type III Stress Urinary Incontinence: Importance of Proper Diagnosis and Treatment," Gynecology and Obstetrics, pp. 473-476.

Conquy, Dophle, "Le point sur L'incontinence urinaire," Expertise et practiques en urologie, No. 3, 1998.

DeLancey, John, "Structural support of the urethra as it relates to stress urinary incontinence: the hammock hypothesis," Am. J. Obstetrics and Gynecology, vol. 170, No. 6, Jun. 1994, pp. 1713-1723.

Gittes et al., "No-incision pubovaginal suspension for stress incontinence," The J. of Urology, vol. 138 (1987), pp. 568-570.

Ingelman-Sundberg, "Surgical treatment of female urinary stress incontinence," Contr. Gynec. Obstet., vol. 10 pp. 51-69 (1983).

Klutke et al., "The anatomy of stress incontinence: magnetic resonance imaging of the female bladder neck and urethra," The J. or Urology, vol. 149, pp. 563-567 (1990).

Leach et al., "Female stress urinary incontinence clinical guidelines panel summary report on surgical management of female stress urinary incontinence," Am. Urological Assc., vol. 158, 875-880 (1997).

Parra et al., "Experience with a simplified technique for the treatment of female stress urinary incontinence," British J. of Urology, vol. 68:615-617 (1990).

Petros et al., "Cough transmission ratio: an indicator of suburethral vaginal wall tension rather than urethral closure?", Acta Obstet Gynecol Scand, 69 Suppl. 153:43-51 (1990).

Petros et al., "Cure of stress incontinence by repair of external anal sphincter," Acta Obstet Gynecol Scand, 69 Suppl. 153:75 (1990).

Petros et al., "Urethral pressure increase on effort originates from within the urethra, and continence from musculovaginal closure," Neurourology and Urodynamics, 14:337-350 (1995).

Petros et al., "An integral theory of female urinary incontinence," Acta Obstet Gynecol Scand, 69 Suppl. 153:7-31 (1990).

Petros et al., "An anatomical basis for success and failure of female incontinence surgery," Scand. J. Urol. Nephrol. Suppl. No. 153:55-61 (1993).

Seim et al., "A study of female urinary incontinence in general practice," Scand. J. Urol. Nephrol 30;465-471 (1996).

Stamey, Thomas, "Endoscopic suspension of the vesical neck for urinary incontinence in females," Am. Surg. pp. 465-472 (1980).

Stanton et al., "Surgery of female incontinence," ch. 7, pp. 105-115.

Ulmsten et al., "The unstable female urethra," Am. J. Obstet & Gynecol. vol. 144, No. 1 (1982).

Ulmsten et al., "Different biochemical composition of connective tissue in continent and stress incontinent women," Acta Obstet. Gynecol. Scand. 66:455-457 (1987).

Ulmsten et al., "Female urinary incontinence—a symptom, not a urodynamic disease. Some theoretical and practical aspect of the diagnosis a treatment of female urinary incontinence," Int. Urogynecology J. 6:2-3 (1995).

Ulmsten et al., "An ambulatory surgical procedure under local anesthesia for treatment of female urinary incontinence," Int. Urogynecology J. 7:81-86 (1996).

Webster, George, "Female Urinary Incontinence," Urologic Surgery, 3rd Ed., pp. 665-680 (1983).

* cited by examiner

URETHRAL STENT SYSTEM AND METHOD

PRIORITY

This application claims priority to and the benefit of U.S. Provisional Patent Application No. 61/445,699, filed Feb. 23, 2011 and entitled "Incontinence Stent System," which is incorporated herein by reference in its entirety.

FIELD OF THE INVENTION

The present invention relates generally to surgical methods and apparatus and, more specifically, to urethral stent systems and methods.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

Some patients can not receive other innovative or conventional sling or like incontinence procedures due to contraindications associated with general anesthesia, anticoagulant therapy, or other surgical solutions and approaches.

As such, there is a desire to obtain a minimally invasive yet highly effective system and method that can be used to treat urinary incontinence.

SUMMARY OF THE INVENTION

The present invention describes pelvic incontinence stents adapted to treat various forms of incontinence in males and females. Embodiments of the present invention are generally directed for use in patients experiencing incontinence and contraindication for other surgical interventions or procedures.

A urethral stent device can include a mechanical valve system, to be delivered up through the urethra via a flexible delivery tool. Embodiments can include a passive valve system adapted to open when exposed to a certain amount of intraluminal pressure and will generally remain open until a desired cessation of fluid flow is achieved. Other embodiments of the valve mechanism or system can be actuated via an external mechanism or device (e.g., manual manipulation, electrical, magnetic, electro-mechanical, etc.).

The valve mechanism of the device can include a pivoting valve assembly having a valve flange, a stopper member and a pivot portion. The flange and stopper are operably connected to the pivot portion and can be generally rigid in certain embodiments. The pivot portion can include a biasing member, such as a spring device, adapted to bias the flange toward a first closed portion. Upon reaching a threshold fluid flow pressure on the flange, the flange moves in a first direction against the resistance of the biasing member. This biasing pressure can be set with the tension or bias of the biasing member according to normal sphincter or like muscle resistance or closure tendencies of a normal urinary lumen.

As fluid and pressure builds up along fluid flow path and against the flange, the bias of biasing member resists the flow and continues to promote continence. At a higher threshold flow level (e.g., buildup of urine within the bladder and along the urethra to the device) the flange begins to move until the flange rests against an interior wall portion of the valve mechanism. As the flange moves toward the wall portion, the stopper member correspondingly moves away from its seated position along the seat wall portion. Upon complete pivoting motion of the flange to the wall the stopper member is fully unseated from its original position such that a new fluid flow is permitted through the valve mechanism. Namely, urine flow is permitted to flow through the stent device to permit voiding.

An advantage of the present invention can be seen when a patient can not receive other innovative or conventional sling or like incontinence procedures due to contraindications associated with general anesthesia, anticoagulant therapy, or other surgical solutions and approaches.

DETAILED DESCRIPTION OF PREFERRED EMBODIMENTS

Figure 1:
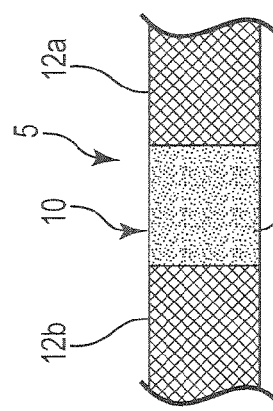
FIG. 1 shows a urethral stent device for use in treating incontinence in accordance with embodiments of the present invention.
Figure 4:
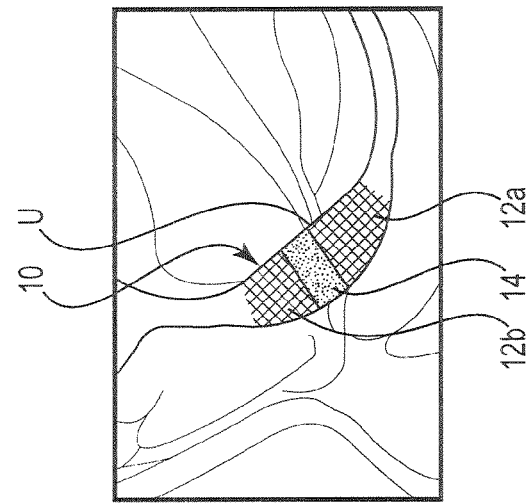
FIGS. 2-6 show various anatomical features and potential deployment sites for a urethral stent device for use in treating incontinence in accordance with embodiments of the present invention.
Figure 3:
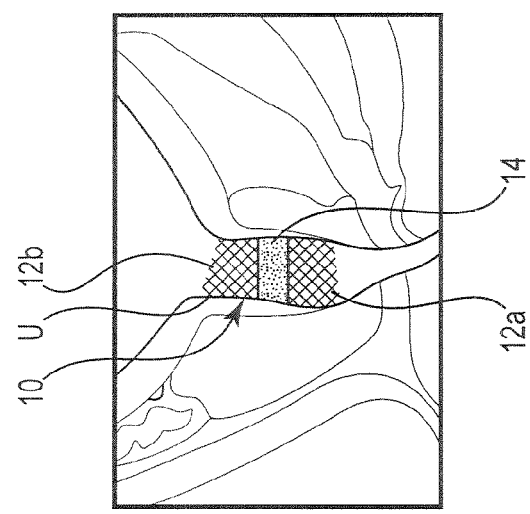
Figure 2:
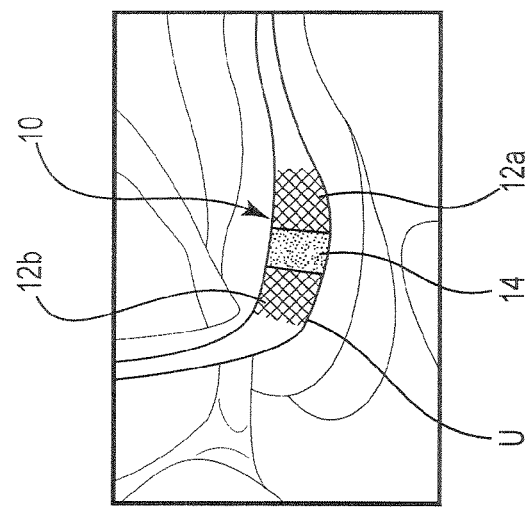
Figure 6:
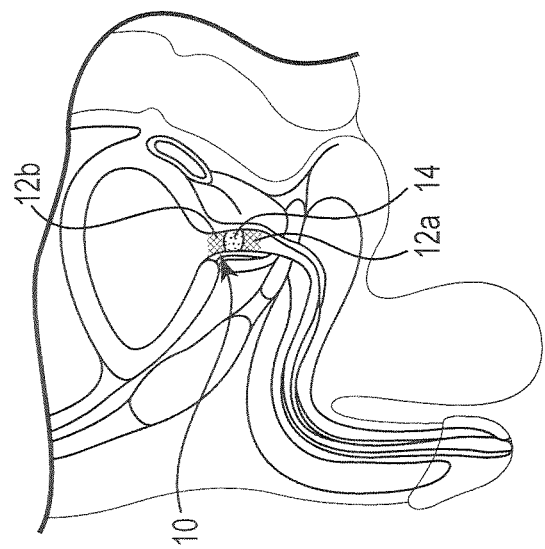
Figure 5:
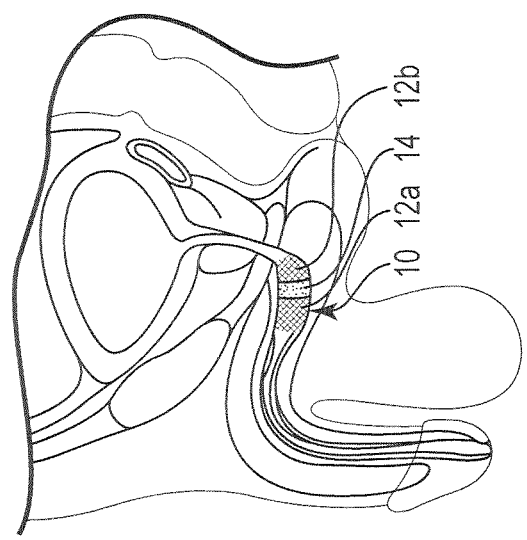

Referring generally to FIGS. 1-9, various embodiments of an implantable stent implant device and system 5 is shown. In general, an implantable stent implant 10 can include a first body portion 12a, a second body portion 12b, and a valve mechanism 14. Various portions of the implant 10 can be constructed of polymer or compatible metal materials, such as polypropylene, polyethylene, fluoropolymers, Nitinol™ or other like materials. The implant device 10 can be constructed at least in part (e.g., portions 12a, 12b) of a biocompatible super alloy mesh tube adapted to provide expansion E along portions (e.g., portions 12a, 12b) of the device 10 due to shape memory properties. Namely, the portions 12a, 12b can self-expand to abut against an interior portion of the urethral wall upon deployment within the body lumen.

The various implants 10, systems, features, devices, introducer and deployment tools, and methods detailed or disclosed (e.g., for male and female) in U.S. Pat. Nos. 7,500,945, 7,407,480, 7,351,197, 7,347,812, 7,303,525, 7,025,063, 6,926,732, 6,991,647, 6,691,711, t,471,718, 6,648,921, 6,612,977, 6,143,021, 5,499,994 and International Patent Publication Nos. WO 2008/057261 and WO 2007/097994, and U.S. Patent Publication Nos. 2010/0105979, 2002/151762 and 2002/147382 are envisioned for use, in whole or in part, with embodiments of the present invention; accordingly, the above-identified disclosures are fully incorporated herein by reference in their entirety. Further, deployment tools and stent devices (e.g., stent expansion characteristics) provided with the UroLume devices and systems, made and sold by American Medical Systems of Minnetonka, Minn., can be employed with the present invention.

FIGS. 2-6 show potential anatomical sites for implantation of the stent device 10 of the present invention. However, the device 10 can be placed along various select portions of the urethral lumen, within male or female patients, to provide continence for the patient while still permitting voiding as disclosed herein.

Figure 7:
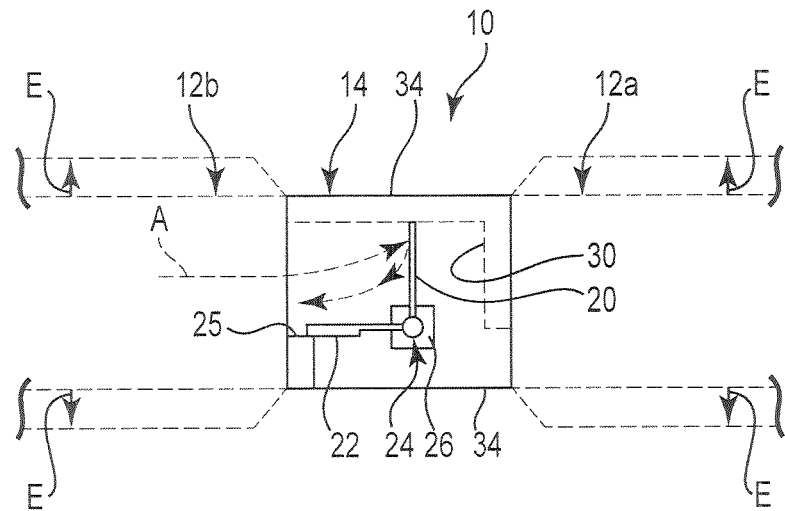
FIG. 7 shows a partial schematic sectional view of a urethral stent device in a closed position in accordance with embodiments of the present invention.
Figure 8:
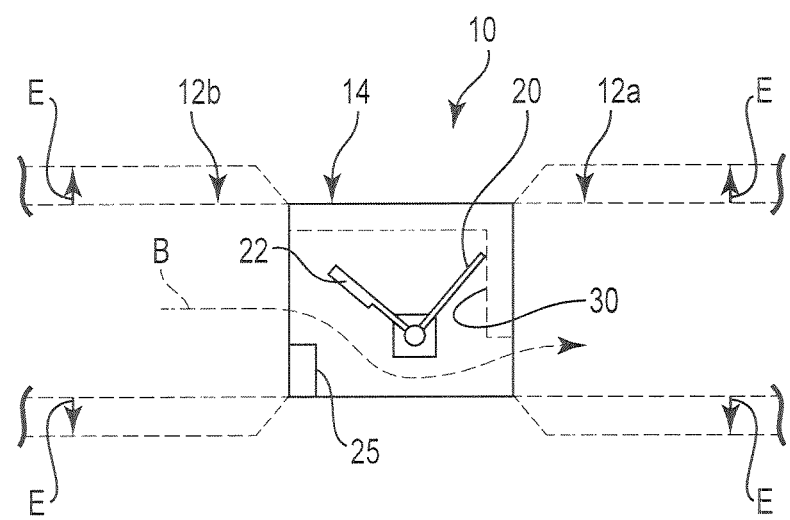
FIG. 8 shows a partial schematic sectional view of a urethral stent device in an open position in accordance with embodiments of the present invention.

Referring generally to FIGS. 7-8, the valve mechanism 14 of the device 10 can include a pivoting valve assembly having a valve flange 20, a stopper member 22 and a pivot portion 24. The flange 20 and stopper 22 are operably connected to the pivot portion 24 and can be generally rigid in certain embodiments. The pivot portion 24 can include a biasing member 26, such as a spring device, adapted to bias the flange toward a first closed portion as shown in FIG. 7. Upon reaching a threshold fluid flow pressure on the flange 20, the flange 20 moves in the direction of or with the flow A, e.g., against the resistance of the biasing member 26. This biasing pressure can be set with the tension or bias of the biasing member 26 according to normal sphincter or like muscle resistance or closure tendencies of a normal urinary lumen.

In general, two primary fluid flow paths are available. Namely, the device 10 is implanted within the urethral lumen of the patient, with the body portions 12a, 12b adapted to expand to securely abut the interior wall of the target urethra portion. Once installed, the valve mechanism 14 defaults in the closed position, as depicted in FIG. 7. The flange 20 is generally sealing against a top wall portion 23 and the stopper member 22 is seated against a seat wall portion 25. As such, urinary flow A or fluid pressure hits the flange 20 but is not sufficient to move the flange 20. As such fluid flow A is not permitted to exit out of the valve mechanism 14 to body portion 12a of the device. This is a state of continence for the patient.

As fluid and pressure builds up along fluid flow A and against the flange 20, the bias of biasing member 26 resists the flow and continues to promote continence. At a higher threshold flow level (e.g., buildup of urine within the bladder and/or along the urethra to the device 10, selective according to the spring or like biasing characteristics of the biasing member 26), the flange 20 begins to move with the flow A and toward the body portion 12a (e.g., at a break open force) until the flange 20 rests against interior wall portion 30 of the valve mechanism 14. As the flange 20 moves toward the wall portion 30, the stopper member 22 correspondingly moves away from its seated position along the seat wall portion 25. Upon complete pivoting motion of the flange 20 to the wall 30, as shown in FIG. 8, the stopper member 22 is unseated from its original position such that a new fluid flow B is permitted through the valve mechanism 14. Namely, urine flow is permitted to flow from the body portion 12b to the body portion 12b via fluid path B to permit voiding through the urethra U. The biasing member 26 or pivoting portion 24 can include a detent mechanism or like mechanisms to facilitate or control release of the spring tension or the break open condition during the pivoting conditions disclosed herein.

Upon completion, or substantial completion, of the voiding process along fluid path B, pressure of the fluid flow reduces to the point where the biasing characteristics of the biasing member 26 can urge the flange 20 back toward its original position, as shown in FIG. 7, to cause a reset of the mechanism 14. As such, the stopper member 25 again reseats at the wall portion 25 and fluid flow along path A is obtained to provide continence for the patient.

As described and depicted, the valve mechanism 14 can be passively actuated according to fluid flow. In other embodiments, the valve mechanism can be actuated (opening or closing—e.g., moving the flange 20 and/or member 22) by external means, including magnetic actuators, electrical actuators, mechanical actuators, electro-mechanical actuators, or other known external triggering sources, devices and techniques.

The valve housing can be a solid or semi-solid assembly. One or more bushings 34 can be included around a periphery or other portion of the valve mechanism 14 to generally reduce or eliminate expansion or movement of the mechanism 14 within the lumen of the urethra U.

Figure 9:
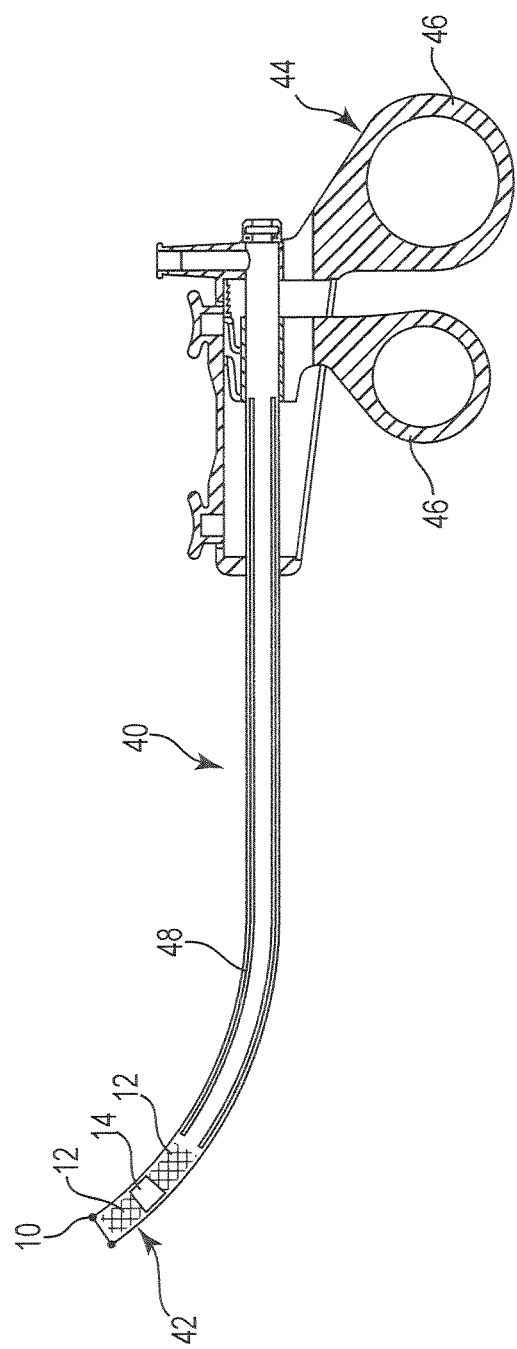
FIG. 9 shows a delivery or introduction tool having a urethral stent device loaded therein in accordance with embodiments of the present invention.

As shown in FIG. 9, various adapted introducer tools 40 can be employed to introduce, deploy and manipulate the stent device 10. The tool 16 can include a distal end 42 adapted to selectively receive or secure the device 10 therein, a handle 44 having one or more actuation portions 46 (e.g., trigger or actuators), and a tubing or shaft portion 48. The tubing or shaft 48 can be generally flexible and in operable communication with the handle 44 and the device 10 to facilitate control and deployment of the device 10 within the urethra of the patient. In certain embodiments, the device 10 is pushed out of the shaft 48 at the distal end 42 once the distal end 42 is inserted and positioned at the target deployment site within the urethra U. While within the tool 40, the device 10 (e.g., portions 12a, 12b) are in a generally compressed configuration. Once deployed from the distal end 42, the device 10, or portions 12a, 12b thereof, automatically expand to provide secure abutment of the device 10 against the interior wall portions of the urethra U to promote continence.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A system for treating urinary incontinence in a patient, comprising:
a stent-like device configured for deployment within a urethra, the stent-like device having;
first and second body portions; and
an interior valve mechanism having a pivoting member including a stopper member, a flange member, and a biasing member, the biasing member including a spring member, the biasing member biasing the pivoting member toward a closed position such that urine flow is at least substantially blocked through the valve mechanism to promote continence, with the stopper member defining a first arm structure and the flange member defining a second arm structure extending at a fixed angle from the stopper member such that the stopper member and the flange member are operably connected to rotate together and the distance therebetween does not substantially change, wherein the valve mechanism is configured such that, during normal operation, the valve mechanism is passively actuated toward an open position when a threshold fluid pressure force is applied to the flange member parallel to a natural direction of urine flow through the urethra without application of an external force.

2. The system of claim 1, wherein at least one of the first and second body portions is constructed of a self-expanding mesh material.

3. The system of claim 1, wherein the first and second body portions are constructed of a self-expanding mesh material.

4. The system of claim 1, wherein the stopper member is provided in an initial seat position to seal off a urine flow path through the valve mechanism when urine flow is at least substantially blocked through the valve mechanism.

5. The system of claim 4, wherein the stopper member is pivotable to an unseated position against the bias of the biasing member to permit urine flow along a flow path through the valve mechanism.

6. The system of claim 1, further including an introducer tool having a catheter portion and a handle actuation portion.

7. The system of claim 6, wherein the catheter portion includes a distal end portion adapted to receive the stent-like device.

8. The system of claim 7, wherein the handle actuation portion is actuated to deploy the stent-like device from the distal end portion of the catheter portion.

9. A system for treating urinary incontinence in a patient, comprising:
a stent-like device configured for deployment within a urethra, the stent-like device having;
first and second self-expanding body portions; and
a single interior valve mechanism having a single pivoting flange member, a single pivoting stopper member, and a biasing member, the biasing member biasing the stopper member toward a closed position such that urine flow is at least substantially blocked through the valve mechanism to promote continence, wherein the pivoting stopper member defines an arm structure that extends generally perpendicular from the pivoting flange member such that the pivoting stopper member correspondingly rotates with the pivoting flange member such that the distance between the pivoting stopper member and the pivoting flange member remains substantially constant and does not decrease, wherein the biasing member is positioned at a pivot point around which the pivoting flange member and the pivoting stopper member pivot.

10. The system of claim 9, further including an introducer tool having a catheter portion and an actuation portion.

11. The system of claim 10, wherein the catheter portion includes a distal end portion adapted to receive the stent-like device.

12. The system of claim 11, wherein the actuation portion is actuated to deploy the stent-like device from the distal end portion of the catheter portion.

13. The system of claim 9, wherein the biasing member includes a spring member.

14. A system for treating urinary incontinence in a patient, comprising:
a stent-like device configured for deployment within a urethra, the stent-like device having;
first and second self-expanding body portions; and
an interior valve mechanism having a pivoting flange member, a pivoting stopper member, and a biasing member, the biasing member biasing the stopper member toward a closed position such that urine flow is at least substantially blocked through the valve mechanism to promote continence, wherein the pivoting stopper member defines an arm structure that extends generally perpendicular from the pivoting flange member such that the pivoting stopper member correspondingly rotates with the pivoting flange member such that the distance between the pivoting stopper member and the pivoting flange member remains substantially constant and does not decrease, wherein the biasing member is positioned at a pivot point around which the pivoting flange member and the pivoting stopper member pivot, wherein the stopper member is configured to be pivotable to a second position when a threshold urine flow pressure is exerted on the flange member such that the stopper member is pivoted to an unseated position to permit urine flow along a flow path through the valve mechanism.

* * * * *